US009872376B2

(12) United States Patent
Burton et al.

(10) Patent No.: US 9,872,376 B2
(45) Date of Patent: Jan. 16, 2018

(54) MEDICAL LINEAR ACCELERATOR SIGNAL ANALYZER AND DISPLAY DEVICE

(75) Inventors: Bradley Burton, Livermore, CA (US); Pierre Mallia, Las Vegas, CA (US); Jay Brown, Mountain View, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 986 days.

(21) Appl. No.: 13/251,092

(22) Filed: Sep. 30, 2011

(65) Prior Publication Data

US 2013/0085702 A1    Apr. 4, 2013

(51) Int. Cl.
| | |
|---|---|
| *H05H 9/00* | (2006.01) |
| *A61B 5/055* | (2006.01) |
| *A61B 5/107* | (2006.01) |
| *G21K 1/12* | (2006.01) |
| *A61N 5/10* | (2006.01) |

(52) U.S. Cl.
CPC ........... *H05H 9/00* (2013.01); *A61B 5/055* (2013.01); *A61N 5/1048* (2013.01); *A61N 5/1075* (2013.01); *G21K 1/12* (2013.01); *H05H 2277/11* (2013.01)

(58) Field of Classification Search
CPC ...... H05H 9/00; H05H 2277/11; G06F 19/00; G21K 1/12; A61B 6/00; A61B 5/055
USPC .................................................... 702/108
See application file for complete search history.

(56) References Cited

U.S. PATENT DOCUMENTS

| | | | | |
|---|---|---|---|---|
| 6,242,747 | B1 * | 6/2001 | Sugitani et al. | 250/396 R |
| 6,556,202 | B1 * | 4/2003 | Taraki | G01R 13/0227 |
| | | | | 345/440 |
| 7,081,750 | B1 * | 7/2006 | Zhang | 324/309 |
| 7,455,542 | B2 * | 11/2008 | Norwood et al. | 439/315 |
| 2002/0128786 | A1 * | 9/2002 | Alexander | G01R 29/02 |
| | | | | 702/66 |
| 2003/0072411 | A1 * | 4/2003 | Welsh | A61N 5/1048 |
| | | | | 378/65 |

(Continued)

OTHER PUBLICATIONS

Adams et al., A Radiation Hardened High Voltage 16:1 Analog Multiplexer for Space Applications (NGCP3580), 2008 IEEE Radiation Effects Data Workshop, Tucson, AZ, 2008, pp. 82-84.*

(Continued)

*Primary Examiner* — Gregory J Toatley
*Assistant Examiner* — Michael Dalbo (57) ABSTRACT

A method and system is proposed for providing automated, electronic testing of a linear accelerator from a remote position. According to one aspect of the claimed subject matter, a system is described which includes a linear accelerator with a scope circuit board, a multiplexer printed circuit board and a computing device. The multiplexer printed circuit board is coupled to the linear accelerator at a plurality of signal sites or locations corresponding to common areas of interest. Signal data received by the multiplexer circuit board may be continuously streamed from the linear accelerator to the multiplexer through each "channel" of data. The multiplexer circuit board is configured to receive, as input, the data corresponding to the electrical activity. In a further embodiment, the multiplexer outputs a selection of signals corresponding to a user selection of one or more channels from a remote terminal.

36 Claims, 5 Drawing Sheets (56) References Cited

U.S. PATENT DOCUMENTS

| | | | | |
|---|---|---|---|---|
| 2003/0135340 | A1* | 7/2003 | Cake | G06F 8/34 |
| | | | | 702/68 |
| 2004/0162041 | A1* | 8/2004 | Ferguson | G01R 13/22 |
| | | | | 455/127.2 |
| 2004/0264633 | A1* | 12/2004 | Kamimura et al. | 378/19 |
| 2006/0031031 | A1* | 2/2006 | Cohn | G01R 13/0254 |
| | | | | 702/66 |
| 2006/0119537 | A1* | 6/2006 | Vong | G06F 1/1601 |
| | | | | 345/1.3 |
| 2006/0230447 | A1* | 10/2006 | Buchholz | 726/17 |
| 2006/0273746 | A1* | 12/2006 | Delaperriere | A61N 5/1048 |
| | | | | 315/501 |
| 2007/0041496 | A1* | 2/2007 | Olivera | A61N 5/103 |
| | | | | 378/65 |
| 2008/0048750 | A1* | 2/2008 | Fujita et al. | 327/276 |
| 2008/0228445 | A1* | 9/2008 | Hamilton | G01R 13/0236 |
| | | | | 702/189 |
| 2010/0146049 | A1* | 6/2010 | Smychliaev | H04L 12/1818 |
| | | | | 709/204 |
| 2011/0121763 | A1* | 5/2011 | Sadler | H05H 9/00 |
| | | | | 315/505 |
| 2012/0051665 | A1* | 3/2012 | Adams et al. | 382/294 |
| 2012/0078503 | A1* | 3/2012 | Dzubay et al. | 701/410 |
| 2012/0256762 | A1* | 10/2012 | Greenberger | 340/870.03 |

OTHER PUBLICATIONS

Das et al. "Accelerator beam data commissioning equipment and procedures: Report of the TG-106 of the Therapy Physics Committee of the AAPM", Med. Phys. 35 "9 . . . , Sep. 2008, pp. 4186-4215.*

* cited by examiner

MEDICAL LINEAR ACCELERATOR SIGNAL ANALYZER AND DISPLAY DEVICE

TECHNICAL BACKGROUND

The development of medical linear accelerators (linacs) has dramatically increased the practicality and efficiency of multi-field radiation therapy treatments. However, like many other complex systems, linear accelerators are subject to decreased efficiency or malfunction due to various causes. These causes may include, for example, damage or defects attributable to malfunctioning subcomponents or environmental factors. For example, as heavy consumers of electrical power, medical linear accelerators may be vulnerable to defective or compromised power sources. This may result in ineffective or inefficient operation of the linear accelerator.

Traditional methods of diagnosing and solving such problems, known as "troubleshooting," often include usage of an oscilloscope. Oscilloscopes are a type of electronic test instrument which, when coupled (via probes) to an area exhibiting radio frequency or electrical activity (e.g., with an electric current, frequency, and/or voltage), generate a graphical display of the electrical activity, typically as a two-dimensional graph of one or more characteristics of the electrical activity plotted as a function of time. These graphical displays allow a technician to diagnose the defective component or source of malfunction, typically through the process of elimination.

Under traditional techniques for troubleshooting a linac, a field service representative would be required to be present at the location of the linear accelerator with a portable oscilloscope. Once in physical proximity with the linear accelerator, the field service representative would be required to manually connect the probes of the oscilloscope to areas of interest (e.g., power supply) of the linear accelerator. In a typical linear accelerator, there may be up to 16 or more areas of interest, corresponding to major components, sub-components, and the connections between of the linear accelerator. Unfortunately, typical oscilloscopes are equipped with only a few (e.g., two or four) probe devices. Oscilloscopes with even greater probes are exponentially more expensive. This requires that the field service representative manually reposition the oscilloscope probes to correspond to the areas of interest for each area of interest in excess of the number of probes, or sacrifice tremendous cost-effectiveness. Naturally, this can be an extremely user intensive process due to the effort and expertise required to manually reposition the oscilloscope probes. Even with more expensive oscilloscopes, such practice can result in significant delays—particularly to remote linear accelerators—due to the time required to travel to the linear accelerator site, and even then, connecting each probe to the areas of interest for each service operation—and each linear accelerator—can result in extremely compromised efficiency.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

As a solution to the problems noted above inherent in traditional linear accelerator testing, a method and system is proposed for providing automated, electronic testing of a linear accelerator from a remote position. According to one aspect of the claimed subject matter, a system is described which includes a linear accelerator with a scope circuit board, a multiplexer printed circuit board and a computing device. The multiplexer printed circuit board is coupled to the linear accelerator at a plurality (for example, 16 or more) of signal sites or locations corresponding to common areas of interest. These areas of interest may include, for example, connection terminals between components and sub-components, or input terminals connected to power sources. Signal data received by the multiplexer circuit board may be continuously streamed from the linear accelerator to the multiplexer through each "channel" of data. The multiplexer circuit board is configured to receive, as input, the data corresponding to the electrical activity (e.g., voltage, frequency, and/or current) at each of the areas of interest. In a further embodiment, the multiplexer outputs a selection of signals corresponding to a user selection of one or more channels. For example, a user is able to select two signal channels (e.g., through a remotely generated instance of a user interface).

The multiplexer then outputs the signal data corresponding to the user-selected channels into a scope board which formats the signal data (analog) into digital display data. In still further embodiments, the scope board is coupled to an input/output communications device, such as a computing device configured to connect to a network, such as a local area network (LAN), wide area network (WAN), or the Internet. The display data is accessible to instances of an associated user interface executing on a remotely located computing system through the network. According to one embodiment, a remote computing system may be required to successfully complete an authorization protocol to access the display data on the communications device. Thereafter, the display data may be graphically represented on a display device coupled to the computing system. In still further embodiments, the user is able to select a different set of signal channels, and/or manipulate a plurality of control operations to modify display parameters to reformat the display data as desired through the instance of the user interface. For selections of signal channels, the user input is relayed to the multiplexer, which automatically conforms (i.e., selects) the output according to the user selection. Likewise, for modifications to display parameters, the user input is relayed to the scope board which automatically reformats the signal data into display data according to the display parameters. Accordingly, such a system allows an emulation of troubleshooting via on-site diagnosis with an oscilloscope through remote, secure interfaces, while avoiding the traditional requirements of on-site proximity and/or manual adjustment of probed sites.

According to another aspect of the claimed subject matter, a method is provided to facilitate the remote, automated emulation of oscilloscope-aided diagnosis. This method includes verifying an authorization of a remote user to access signal data generated by a linear accelerator. Once authorization is verified, a scope board and multiplexer circuit board coupled to the linear accelerator are initialized to pre-set configuration values. User input (corresponding to a selection of signal channels and/or a plurality of display parameters) is received, through a communications device for example, and relayed to the appropriate destination. Signal data from selected channels is output and formatted according to the indicated display parameters into digital display data, which is then forwarded by the communications device to the user interface of the remote user. Subsequent user-initiated adjustments may be automatically performed by the scope board and multiplexer circuit board as necessary, with the resultant formatted display data being relayed to the user.

A final aspect of the claimed subject matter includes program instructions contained on computer readable media, such as non-transitory computer readable media. These program instructions may be computer executable, and, when executed, provide instructions to: establish a connection with a remote communications device of a linear accelerator; receive display data generated by a scope board of the linear accelerator from signal data relayed to the scope board by a multiplexer circuit board; graphically render the display data in a display device; relay user input corresponding to a user-selection of signal data sources and/or modifications to the display parameters to the appropriate linear accelerator component; and receive and display subsequent reformatted and/or re-sourced display data from the linear accelerator.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known processes, procedures, components, and circuits have not been described in detail as not to unnecessarily obscure aspects and features of the subject matter.

Portions of the detailed description that follow are presented and discussed in terms of a process. Although operations and sequencing thereof are disclosed in a figure herein (e.g., FIG. 4) describing the operations of this process, such operations and sequencing are exemplary. Embodiments are well suited to performing various other operations or variations of the operations recited in the flowchart of the figure herein, and in a sequence other than that depicted and described herein.

Some portions of the detailed description are presented in terms of procedures, operations, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed operation, logic block, process, etc., is here, and generally, conceived to be a self-consistent sequence of operations or instructions leading to a desired result. The operations are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While the following example configurations are shown as incorporating specific, enumerated features and elements, it is understood that such depiction is exemplary. Accordingly, embodiments are well suited to applications involving different, additional, or fewer elements, features, or arrangements.

Exemplary Remote Linear Accelerator Diagnostic System

Figure 1:
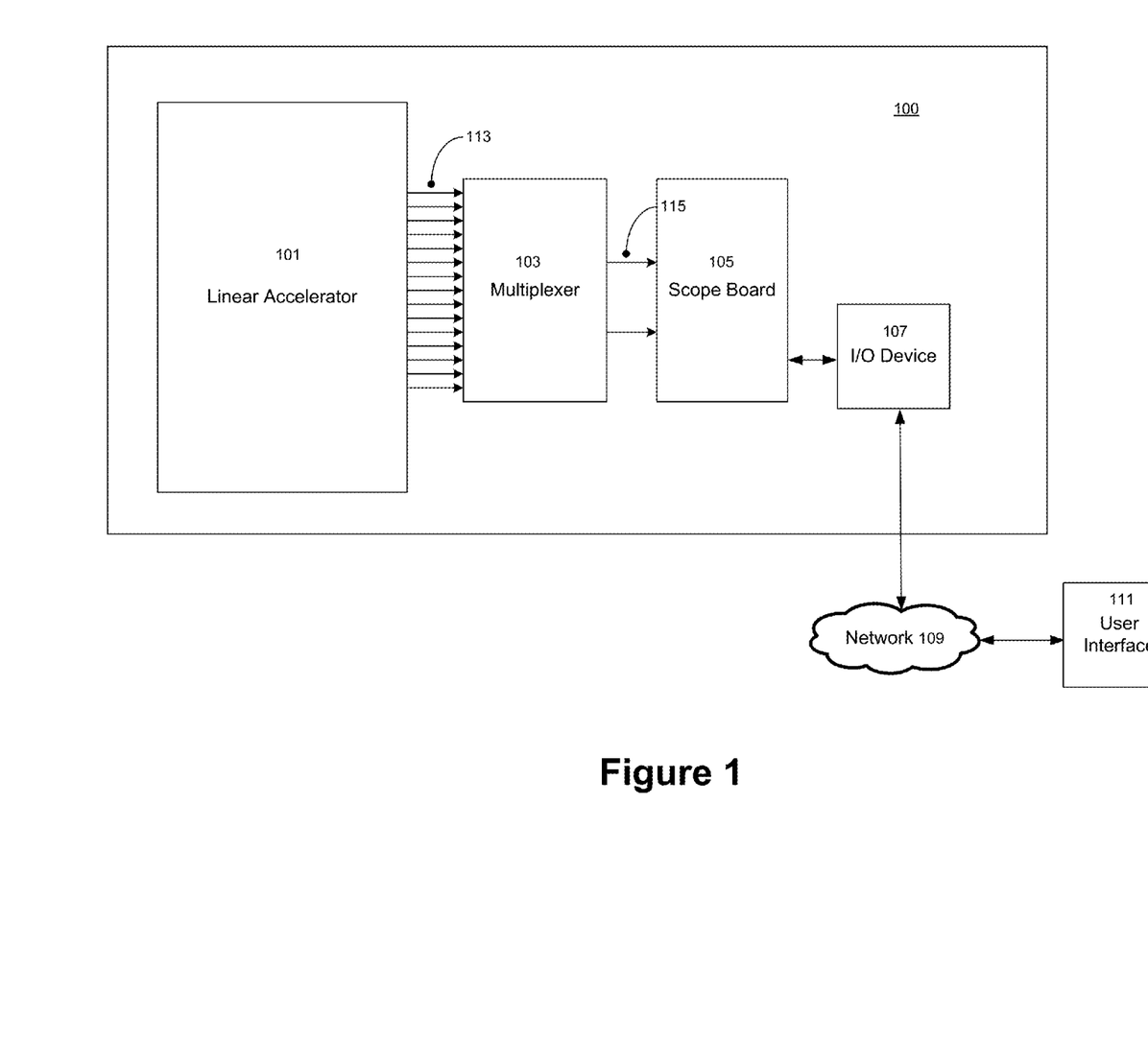
FIG. 1 depicts a block diagram of an exemplary system for performing remote linear accelerator diagnostics, in accordance with embodiments of the present invention.

With reference now to FIG. 1, a block diagram of an exemplary remote linear accelerator diagnostic system 100 is depicted, in accordance with one embodiment. In one configuration, remote linear accelerator diagnostic system 100 includes a linear accelerator 101, multiplexer 103, scope board 105 and Input/Output device 107. As depicted, system 100 presents a combination of proximately located and coupled components. System 100 may be externally accessed by an instance of a user interface 111 executed on a remote computing system via a network 109.

In an embodiment, the multiplexer 103 may be implemented as a radiation-resistant multiplexer printed circuit board, and is statically coupled to the linear accelerator 101 at a plurality of areas of interest. These areas of interest may consist of connection terminals, wires, or other mediums and sites exhibiting or conducting electrical or radio frequency (RF) activity. These areas of interest may be distributed throughout the major components and sub-components of the linear accelerator, and may be located at popular or frequent diagnosis sites. Such components may include, for example, but are limited to, one or more vacuum chambers, a particle source, a power source, amplifiers, etc. In further embodiments, each of the plurality of areas of interest are coupled to the multiplexer 103, which receives the signal data (e.g., data corresponding to the electrical or RF activity) of each of the areas of interest. Signal data may comprise the raw analog representations of the frequency, amplitude, current, voltage of the electric or radio frequency activity at the area of interest. In still further embodiments, the signal data is produced in a continuous stream in data channels (113) corresponding to each area of interest. According to one embodiment, each area of interest in the linear accelerator 101 is physically coupled by a cable—such as a coaxial cable—to input terminals of the multiplexer 103. In an embodiment, the input terminals of the multiplexer 103 are implemented as Bayonet Neill-Concelman Radiofrequency (BNC) connectors. The number of inputs on the multiplexer 103 may vary. In some embodiments, the number of inputs (e.g., signal channels) may be upwards of or even exceed 16, representing the 16 most common and/or critical signal areas of the linear accelerator.

In some embodiments, the multiplexer 103 contains logic to select a set of signal channels from the plurality (e.g., 16) of signal channels. According to one implementation, the multiplexer 103 selects one or more signal channels from the plurality of signal channels to output. Multiplexer 103 may be configured to route one or more signal channels based on a user-supplied input indicative of a user-selection to output. In one embodiment, the user-supplied input is supplied at a remote user interface 111, and relayed to the multiplexer 103. According to some embodiments, the multiplexer 103 may be configured to output a default set of signal channels or no channels at all, until user selection of signal channels is received. Output (e.g., analog or digital signal data) from the multiplexer 103 is received in a scope board 105 (implemented as a scope printed circuit board, for example) which may be physically coupled to the multiplexer 103. In an embodiment, the signal data may be transferred from the multiplexer 103 to the scope board 105 via coaxial cables (115) at BNC connector terminals on the scope board 105.

The scope board 105 receives the signal data from the multiplexer 103 corresponding to the set of signal channels. In an embodiment, the signal data consists of raw analog data. According to such embodiments, the scope board 105 may include an analog to digital converter, which it uses to convert the analog signal data to digital data. The scope board 105 formats the digital data for display (e.g., as waveforms) in a user interface (such as user interface 111). In some embodiments, formatting the digital data may include applying display parameters to the display data. Display parameters may consist of the length of time during which signal data is displayed, triggering events corresponding to the signal data, or data offsets corresponding to specific activity or regions of interest in a display generated from the display data. The data offsets may be used, for example, to focus a display on a specific period of time, a specific event or activity, or a graphically produced region of interest. Focusing may be implemented as, for example, "zooming" (artificially amplifying) into an area of a signal graph in a graphical representation. Once formatted in the scope board 105, the display data is communicated to an input/output (I/O) device 107 in the system 100. The input/output device 107 may comprise, or be comprised in, for example, a local computing device communicatively coupled to the scope board 105. In one embodiment, the scope board 105 is coupled to the I/O device 107 via a Universal Serial Bus (USB) connection.

As depicted in FIG. 1, the I/O device 107 may be coupled to a network 109 (via an ethernet or like data communication protocol, for example). Network 109 may be implemented as a local area network, a wide area network, or a public domain (Internet). According to one aspect of the claimed subject matter, a remotely located terminal, such as an instance of a user interface 111 executing on computing device remotely located from the linear accelerator 101, is able to access the display data and manipulate the multiplexer 103 and scope board 105 to adjust the signal data and/or the display data. Access may be granted to remotely executing user interfaces 111 via a communicatively coupling facilitated over the network 109. According to further embodiments, remote devices (e.g., user interface 111) seeking access to the display data may be granted access only upon successful authorization according to an authorization protocol. This authorization protocol may be executed at I/O device 107, for example, and may be consistent with standard network-based authorization procedures.

Figure 2:
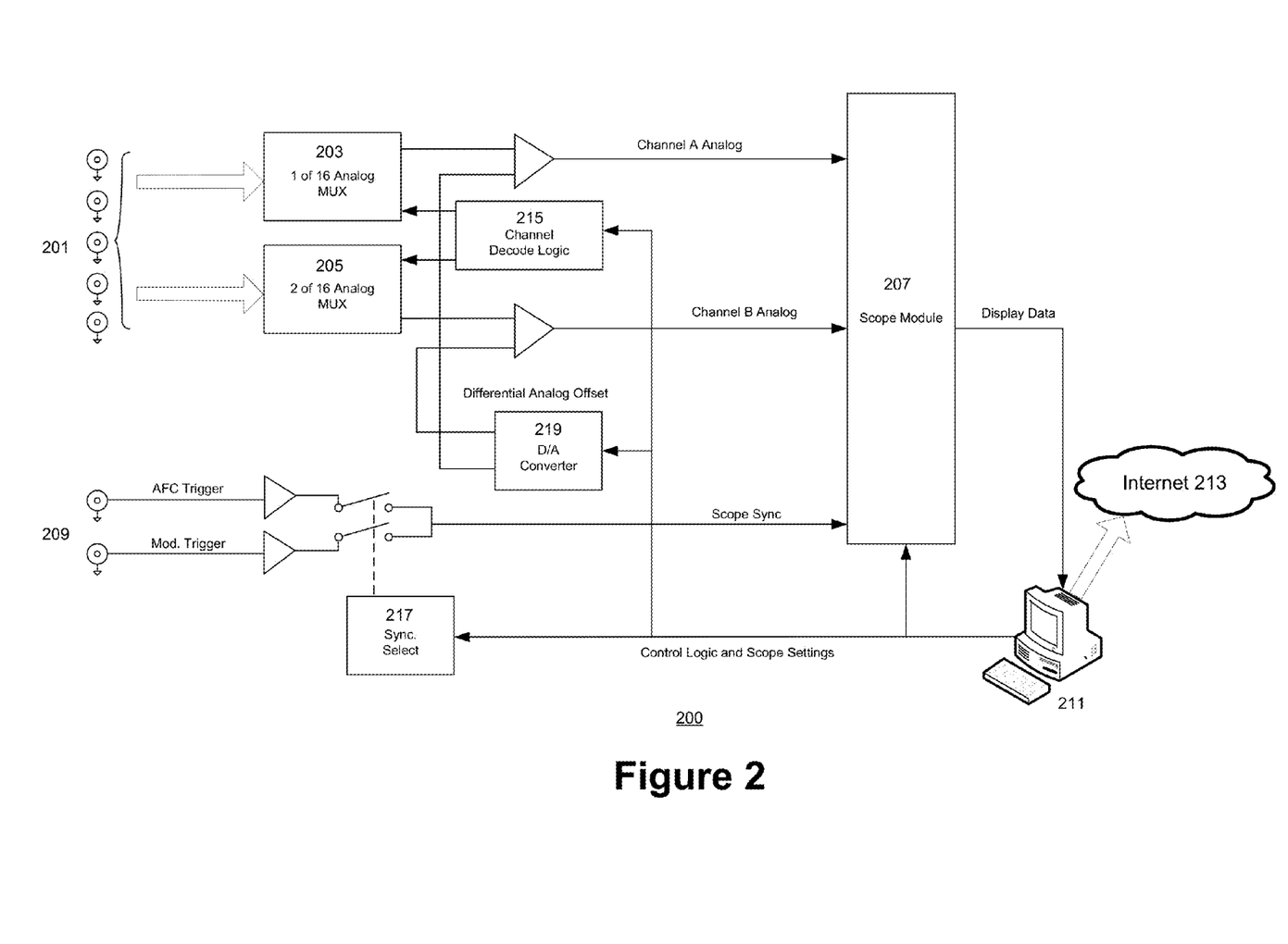
FIG. 2 depicts a system diagram of an exemplary system for performing remote linear accelerator diagnostics, in accordance with embodiments of the present invention.

With reference now to FIG. 2, a state diagram 200 of an exemplary remote linear accelerator diagnostic system is depicted, in accordance with one embodiment. State diagram 200 presents the flow of data between and through a plurality of system states in a remote linear accelerator diagnostic system. As presented in FIG. 2, state diagram 200 includes a plurality of analog channels 201 corresponding to a plurality of electrical and/or RF signals from a linear accelerator. The signals may correspond to connection terminals and/or wires within and between the various component and sub-component sub-systems comprised in the linear accelerator. According to an embodiment, analog channels 201 may consist of 16 or more analog channels coupled to the 16 (or more) most critical or popular areas of interest of the linear accelerator. The analog channels 201 output raw (analog) signal data into inputs of a multiplexer. The multiplexer contains logic to select a set of the analog channels 201 to output from its output terminals (e.g., MUX output terminal 203, 205). This logic may use, for example, user supplied logic (supplied digitally from an external source), which it decodes in channel decode logic 215. Once the set of channels is selected to be output from the multiplexer, each channel is separately output and received in a scope module 207.

In one embodiment, the multiplexer is configured to output two channels (represented in FIG. 2 as Channel A Analog and Channel B Analog). The analog channel data received from the multiplexer outputs 203, 205 is converted into digital display data in scope module 207, and subsequently transmitted to a proximate I/O device (e.g., computing device 211). In an embodiment, the analog data is received from the linear accelerator through the plurality of analog channels 201 by multiplexer in a continuous stream. According to such embodiments, the signal data is similarly output from the multiplexer through the multiplexer outputs 203, 205 continuously. As such, the scope module 207 converts the analog signal data into the digital display data similarly in a continuous stream, as the signal data is received. The stream of display data is accessible to authorized users via established network connections with the I/O device 211. These network connections may include connections established with data communication protocols (e.g., TCP/IP, HTTP) over local area, wide area, and public networks 213.

Authorized users may also be able to select alternate analog channels from the plurality of analog channels 201 to display as display data. In addition, authorized users may be able to submit display parameters to adjust the format (appearance) of the display data. User supplied selections of analog channels 201 to display may be communicated digitally. As such, the user input may be converted to an analog signal in digital-analog converter 219, comprised in the multiplexer. Channel decode logic 215 may, as previously discussed, decode the user input and be used to select the particular analog channel(s) to output. Display parameters may include establishing events which begin the display of electric or RF activity. These events, known as "triggers" may be supplied by the remote user, synchronized to the relayed signal data by synch module 217 and applied via trigger channels 209 in the scope module.

Exemplary User Interface

Figure 3:
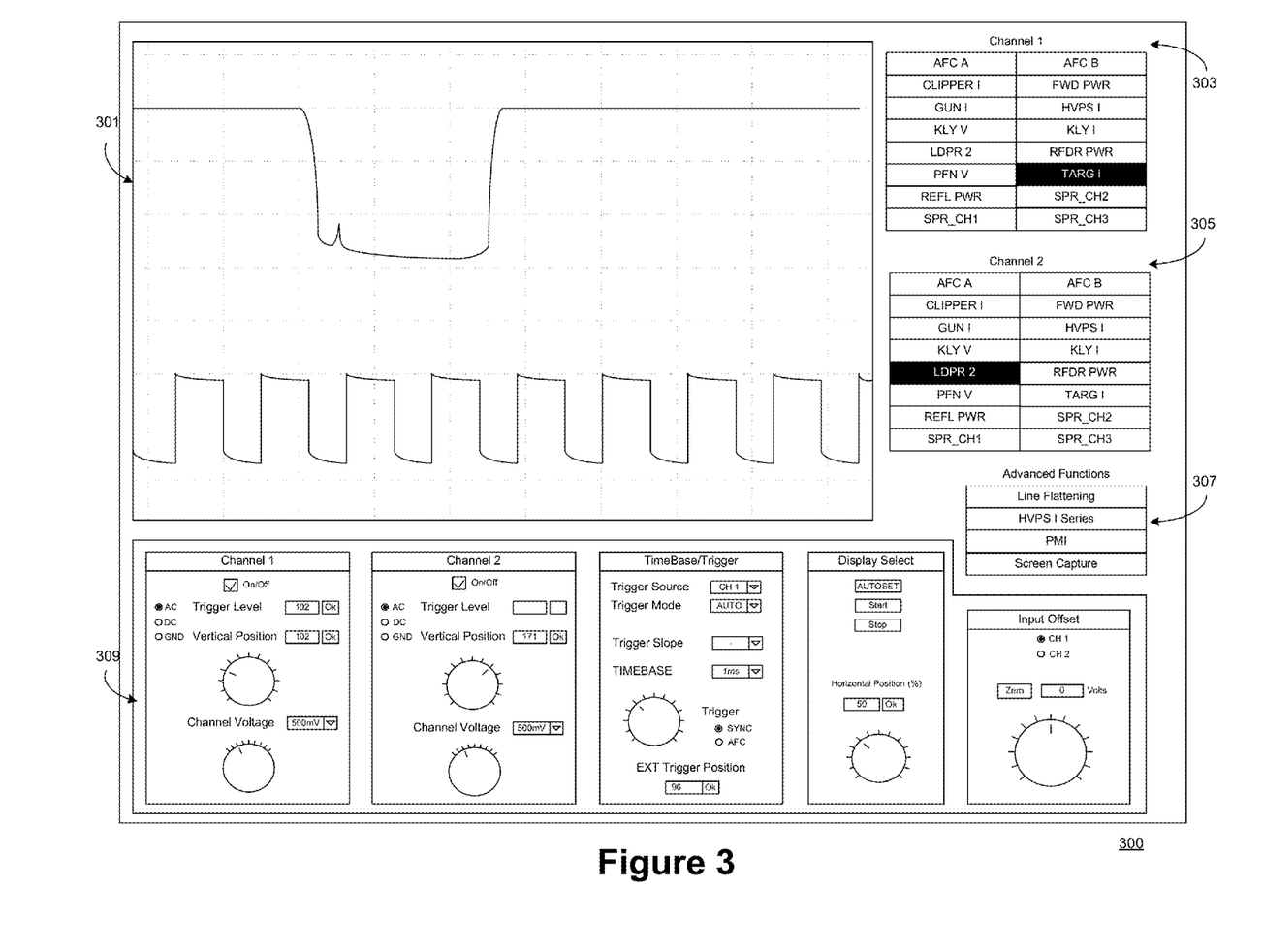
FIG. 3 depicts an illustration of an exemplary user interface generated by a system for performing remote linear accelerator diagnostics, in accordance with embodiments of the present invention.

With reference now to FIG. 3, an illustration of an exemplary user interface 300 is depicted, in accordance with an embodiment. In one configuration, user interface 300 is generated by a computing system remotely located from a linear accelerator to provide oscilloscope emulation and diagnostic tools remotely. As presented in FIG. 3, user interface 300 includes a graphical display area 301, and a plurality of user-input fields which may be graphically implemented as, for example buttons, fields, menus, knobs, etc. (e.g., channel selection menus 303, 305; advanced function menu 307, Control Panel 309). In one embodiment, display data for a set of signals received through a network-connection from an I/O device of a linear accelerator (such as computing devices 107 and 211 of FIGS. 1 and 2) is graphically represented as waveforms in display area 301. As depicted in FIG. 3, data from a set of two channels is presented in display area 301. In one embodiment, the display area 301 displays a graph of the amplitude of a waveform corresponding to signal data over time. The channels comprising the set of channels may be selected in channel selection menus 303, 305.

Channel selection menus 303, 305 correspond to the channels selected for output from the multiplexer (e.g., multiplexer 103). As presented in FIG. 3, Channel selection menus 303 and 305 each correspond to a separate multiplexer output, and are implemented as a plurality of buttons (e.g., AFC A, AFC B, CLIPPER I, FWD PWR, GUN I, HVPS I, KLY V, KLY I, LDPR 2, RFDR PWR, PFN V, TARG I, REFL PWR, and Spares 1-3 which may be used to connect to any desired terminal), each identified to correspond to a particular connection, component, or specific signal in the linear accelerator. For example, KLY I corresponds to the current of a klystron vacuum tube component in the linear accelerator, whereas KLY V corresponds to the voltage of the klystron vacuum tube. Likewise, HVPS I corresponds to the current (I) of the high-voltage power supply of the linear accelerator.

The plurality of buttons are configured such that a user actuation (representative of a user selection of a signal channel to display) visually distinguishes the button from the other, unselected plurality of buttons. In an embodiment, only one button (e.g., signal channel) per output channel may be selected, and actuation of another button in the selection menu de-selects a previously actuated button in the same output channel. As shown, a selected button may be visually distinguished via color. Other visual distinctions may apply (e.g., font, size, graphical effects, etc.). A user selection of a signal channel to be used as an output channel causes the multiplexer 103 of the remote linear accelerator to output the corresponding signal channel in the output channel selected by the user. Subsequently, signal data from the selected signal channel is routed to the scope board, where the signal data is converted into digital display data and graphically represented in display area 301. In alternative embodiments, a single menu displaying the plurality of buttons for one output channel may be displayed at a time. Alternating between the displays may be performed by selecting a toggle which replaces the menu of a output channel with the menu of another output channel. Where the plurality of output channels is in excess of two, alternating between the displays may be performed by cycling through each menu corresponding to an output channel in sequential order, or, selecting an output channel from a dropdown menu.

According to some embodiments, a linear accelerator diagnostic system such as system 100 is further configured to apply advanced functions which cause a scope board of the linear accelerator to format the display data according to a pre-defined set of configurations. These advanced functions may include, for example, line flattening (shown as "Line Flattening" button in advanced function menu 307), high-voltage power supply (shown as "HVPS I Series" button in advanced function menu 307), aggregate channel view (shown as "PMI" button in advanced function menu 307) and single channel screenshot (shown as "Screenshot" button in advanced function menu 307). User actuation of the line flattening button causes the waveform corresponding to the current of the Klyston vacuum tube (KLY I) in the linear accelerator (and corresponding to channel identified as KLY I) to be displayed as the output for a selected output channel of the multiplexer. The display from other output channel(s) is disabled. User actuation of the high-voltage power supply button causes the waveform corresponding to the current of the high-voltage power supply in the linear accelerator (and corresponding to channel identified as HVPS I) to be displayed as the output for a selected output channel of the multiplexer. The display from other output channel(s) is disabled.

User actuation of the PMI button generates a document—such as a document according to a portable document (".pdf") format—containing an image ("screenshot") captured for the waveforms of each signal channel at that instant. Once actuated, the multiplexer for one output channel cycles through each of the signal channels and stores an image of the waveform at the instant. In one embodiment, the other output channel is not displayed (e.g., no channel is selected) during this time. User actuation of the screen capture button a generates a document—such as a document according to a portable document (".pdf") format—containing an image ("screenshot") captured for the waveforms of the signals currently displayed in the display area 301 at that instant. In further embodiments, the document generated by user actuation of the PMI and/or Screen Capture buttons is automatically time and date stamped with the corresponding information at actuation.

Control Panel 309 allows the user to adjust the display parameters used to format the display data in display field 301. According to further embodiments, Control Panel 309 also provides functionality to the user to set trigger events, alternate the starting position of waveforms and trigger events (e.g., the source, slope and mode of the trigger), and adjust the offset of the data signal input in the display area 301. In some embodiments, Control Panel 309 includes an autoset button, which configures the display data for a signal channel to pre-set configurations specific to each signal channel. Other applicable display parameter modifications include modification of the X and Y axes. For example, the duration of the timebase (e.g., the unit of time for which the signal data is displayed) used as the X-axis, and the degree per unit of amplitude of the waveform used as the Y-axis may be adjusted in Control Panel 309. User input supplied through the Control Panel 309 is relayed to the scope board (e.g., scope board 105, 207). The scope board 105, 207 applies display parameters conforming to the user supplied input during the conversion of the received signal data into display data. In an embodiment, the modifications to the display parameters are applied instantaneously, and the display data streamed from the scope board 105, 207 and graphically displayed in display area 301 is immediately modified according to the user supplied input.

According to some embodiments, once the display data is remotely received and displayed in an instance of the user interface, diagnostic operations may be performed (e.g., by a remote service technician or engineer). In further embodiments, once a diagnostic operation has been performed remotely, messages may be relayed to the linear accelerator through the remote user interface. These messages may be displayed on a local user interface on the linear accelerator corresponding to the diagnosis. For example, the messages may indicate an error in a component of the linear accelerator, or that one or more components or sub components require calibration or repair. In still further embodiments, these messages may be pre-programmed and correspond to signals sent from the remote user interface.

Performing Remote Linear Accelerator Diagnostics

Figure 4:
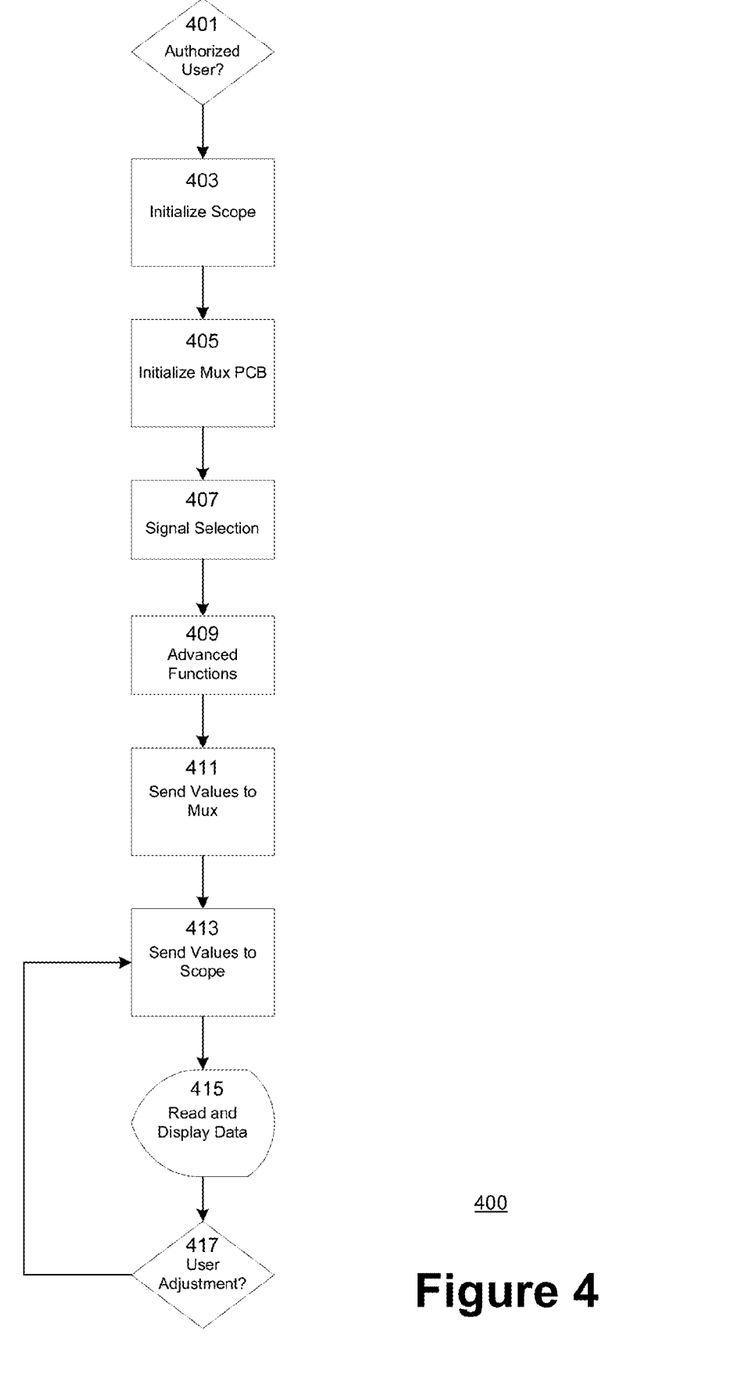
FIG. 4 depicts a flowchart of a method for performing remote linear accelerator diagnostics, in accordance with embodiments of the present invention.

FIG. 4 depicts a flowchart 400 of a method for performing automatic linear accelerator diagnostics, in accordance with one embodiment. Specifically, the method enables the remote emulation of oscilloscope-based diagnostic tools through a networked connection. Steps 401-417 describe exemplary steps comprising the process depicted in flowchart 400 in accordance with the various embodiments herein described. In one embodiment, the flowchart 400 is implemented in whole or in part as computer-executable instructions stored in a computer-readable medium.

At step 401, authorization for a remote user is determined. Authorization may be determined according to standard network protocols, such as querying a requesting user for authorized credentials (e.g., name and password) and verifying the supplied credentials have authorization by referencing a storage of authorized credentials. The authorization protocol may be performed by an I/O device (e.g., computing device 107, 211) proximately coupled to a linear accelerator and configured to receive display data from a scope board (e.g. 105, 207) of a linear accelerator. Once authorized, the process proceeds to steps 403 and 405, which initialize the scope board (e.g., 105, 207) and multiplexer printed circuit board (e.g., multiplexer 103, and 203, 205), respectively. The scope board and multiplexer may be initialized according to pre-set configuration values. Once the scope board and multiplexer are initialized, the process proceeds to step 407.

At step 407, user supplied selection(s) of one or more signal channels and display parameters is received. The signal channels and display parameters may be supplied by the user through an instance of a user interface (e.g., user interface 300) on a remote computing system. The selected channels are directed to the multiplexer which outputs the signal data of the selected channels. Display parameters may be communicated to the scope according to a configuration file which configures the values of the display parameters used by the scope board to format the signal data into display data, based on the user-supplied display parameters. Additionally, user-actuation of advanced functions (e.g., the advanced functions described above corresponding to advanced function menu 307) may be received via user interface 300 at step 409 and communicated to the multiplexer at step 411 and the scope at step 413. Communication of the user-actuated advanced functions may also be communicated according to a configuration file which configures the values of the display parameters used by the scope board to format the signal data into display data.

The signal data and resultant display data is modified, as necessary, at step 415 according to the user-input submitted to the user interface in step 409 and received in the multiplexer and scope at steps 411 and 413, respectively. The resultant display data is also transmitted to and displayed in, the user interface at step 415. Subsequent user input indicative of an adjustment to one or more signal channels or display parameters may be supplied at step 417, which proceeds again to the portion of the process depicted in steps 413 and 415 until no user adjustments are received at step 417.

Exemplary Computing Device

Figure 5:
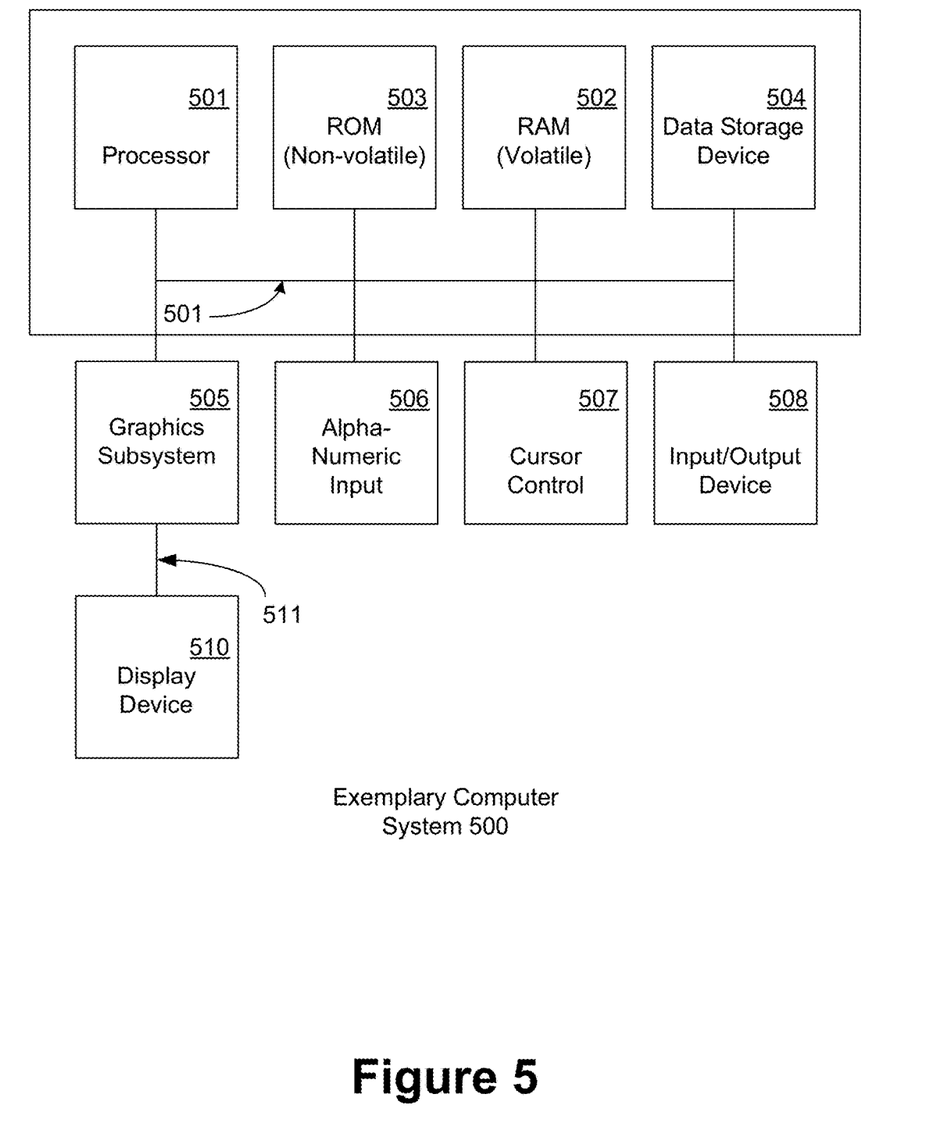
FIG. 5 depicts an exemplary computing system for executing computer readable medium containing instructions to perform remote linear accelerator diagnostics, in accordance with embodiments of the present invention.

As presented in FIG. 5, an example system for implementing embodiments of the presently claimed subject matter is depicted. FIG. 5 includes a general purpose computing system environment, such as computing system 500. In its most basic configuration, computing system 500 typically includes at least one processing unit (CPU) 501 and memory, and an address/data bus 509 (or other interface) for communicating information. Depending on the exact configuration and type of computing system environment, memory may be volatile (such as RAM 502), non-volatile (such as ROM 503, flash memory, etc.) or some combination of the two. In an embodiment, the computing system 500 may be implemented as the physical hardware resource which may be perform program instructions to execute an instance of a user interface and to perform one or more steps of a process to perform remote linear accelerator diagnosis. In a further embodiment, computing system 500 may be one of many associated computing systems in a network.

Computer system 500 may also comprise an optional graphics subsystem 505 for presenting information to the computer user, e.g., by displaying information on an attached display device 510, connected by a video cable 511. In an embodiment, user interface 300 may be generated, in whole or in part, by the graphics subsystem 505, memory (502, 503), and processing unit 501 of computer system 500 to display formatted display data on display device 510. Additionally, computing system 500 may also have additional features/functionality. For example, computing system 500 may also include additional storage (removable and/or non-removable) including, but not limited to, magnetic or optical disks or tape. Such additional storage is illustrated in FIG. 5 by data storage device 504. Computer storage media includes volatile and nonvolatile, removable and non-removable media implemented in any method or technology for storage of information such as computer readable instructions, data structures, program modules or other data. RAM 502, ROM 503, and data storage device 504 are all examples of computer storage media.

Computer system 500 also comprises an optional alphanumeric input device 506, an optional cursor control or directing device 507, and one or more signal communication interfaces (input/output devices, e.g., a network interface card) 508. Optional alphanumeric input device 506 can communicate information and command selections to central processor 501. Optional cursor control or directing device 507 is coupled to bus 509 for communicating user input information and command selections to central processor 501. Signal communication interface (input/output device) 508, also coupled to bus 509, can be a serial port. Communication interface 509 may also include wireless communication mechanisms. Using communication interface 509, computer system 500 can be communicatively coupled to other computer systems over a communication network such as the Internet or an intranet (e.g., a local area network), or can receive data (e.g., a digital television signal). In an embodiment, communication interface 509 may be used to communicate with a remotely located I/O device of a linear accelerator to transmit display data used to generate the user interface displayed in display device 510.

By using any of the systems or methods provided above, a linear accelerator may be securely and accurately diagnosed from a remote terminal, thereby eliminating the need for on-site service and manual repositioning of oscilloscope probes, potentially resulting in improvements to the efficiency and efficacy of linear accelerators diagnostic procedures.

Although the subject matter has been described in language specific to structural features and/or processological acts, it is to be understood that the subject matter defined in the appended claims is not necessarily limited to the specific features or acts described above. Rather, the specific features and acts described above are disclosed as example forms of implementing the claims.

What is claimed is:

1. A linear accelerator diagnostic system comprising:
   a linear accelerator comprising a local user interface;
   a multiplexer circuit board comprising a plurality of input terminals, the input terminals being coupled to the linear accelerator at a plurality of diagnosis sites within the linear accelerator, the multiplexer circuit board being operable to receive signal data from the plurality of diagnosis sites of the linear accelerator as a plurality of inputs and to output a selection of signal data from the signal data;
   a scope board coupled to the multiplexer circuit board, and operable to receive the selection of signal data and to format the received selection of signal data into display data by applying at least one display parameter to the display data;
   a first computing device communicatively coupled to the linear accelerator and configured to receive the formatted display data from the scope board; and
   a second computing device remotely located from the linear accelerator and communicatively coupled to the first computing device through a network, the second computing device comprising a display device, and configured to generate a second user interface to display the display data in the display device and to receive user input corresponding to the display data,
   wherein signal data from a diagnostic site of the plurality of diagnosis sites comprises at least one of: a frequency, an amplitude, a current, and a voltage of electric activity at the diagnostic site,
   further wherein, the local user interface is operable to display diagnostic messages in response to user input received from the second user interface, the diagnostic messages comprising messages pre-programmed in the local user interface.

2. The system according to claim 1, wherein the second computing device is communicatively coupled to the first computing device via the Internet.

3. The system according to claim 1 wherein the plurality of inputs of the multiplexer circuit board from the linear accelerator comprises a plurality of Bayonet Neill-Concelman Radiofrequency (BNC) connectors.

4. The system according to claim 3, wherein the multiplexer circuit board is coupled to the linear accelerator at the plurality of inputs via a coaxial cable.

5. The system according to claim 1, wherein the multiplexer circuit board outputs the selection of signal data to the scope board via a plurality of outputs, the plurality of outputs comprising BNC connectors.

6. The system according to claim 1, wherein the signal data comprises analog data, and wherein the display data comprises digital data.

7. The system according to claim 1, wherein the user interface is configured to receive a plurality of user input corresponding to a plurality of user-supplied signal display control operations, the plurality of user-supplied signal display control operations corresponding to the at least one display parameter.

8. The system according to claim 7, wherein the scope board manipulates the display data to conform to the plurality of user-supplied signal display control operations.

9. The system according to claim 8, wherein the plurality of user-supplied signal display control operations comprises an indication of an area of interest corresponding to a display data.

10. The system according to claim 9, wherein the display data is automatically offset by the scope board to focus on the area of interest.

11. The system according to claim 1, wherein, signal data from each diagnosis site corresponding to the plurality of signal data is continuously streamed to the multiplexer circuit board through a corresponding plurality of signal channels.

12. The system according to claim 11, wherein the selection of signal data comprises a user selection of a set of signal channels comprised in the plurality of signal channels.

13. The system according to claim 1, wherein the first computing device is operable to execute an authorization protocol, wherein access to the display data is granted to the second computing device only when the second computing device successfully navigates the authorization protocol, further wherein the scope board and multiplexer circuit board are initialized to pre-set configuration values when the second computing device successfully navigates the authorization protocol.

14. The system according to claim 1, wherein the plurality of diagnosis sites within the linear accelerator correspond to a plurality of components of the linear accelerator.

15. The system according to claim 14, wherein a diagnosis site of the plurality of diagnosis sites corresponds to a terminal from a group of terminals consisting of:
   a connection terminal between components of the plurality of components; and
   an input terminal between a component and a power source.

16. The system according to claim 1, wherein the display parameter comprises at least one display parameter from the group consisting of:
   a length of time during which signal data is display;
   at least one triggering event corresponding to the signal data;
   at least one data offset corresponding to a specific activity of interest corresponding to a display generated from the display data; and
   at least one data corresponding to a specific region of interest corresponding to a display generated from the display data.

17. The system according to claim 1, further comprising a synch module coupled to the scope board via at least one trigger channel, wherein the synch module is configured to synchronize signal data received in the scope board with trigger events comprised in the at least one display parameter.

18. The system according to claim 1, wherein the user input comprises input corresponding to one or more diagnostic operations.

19. The system according to claim 1, wherein the local user interface is configured to display diagnostic messages in response to a performance of one or more diagnostic operations initiated via the user input received in the second user interface.

20. The system according to claim 1, wherein the pre-programmed, locally stored diagnostic messages are displayed in response to receiving one or more signals received from the second user interface.

21. A method comprising:
   initializing a scope board comprised in a diagnostic system;
   initializing a multiplexer printed circuit board operable to receive signal data from the plurality of diagnosis sites of the linear accelerator and comprised in a linear accelerator of the diagnostic system, the multiplexer printed circuit board comprising a plurality of input terminals coupled to the linear accelerator at a plurality of diagnostic sites within the linear accelerator;
   receiving a selection of signals and a first plurality of display parameters corresponding to user input;
   communicating the selection of signals to the multiplexer printed circuit board and the plurality of display parameters to the scope board;
   generating first display data corresponding to the first selection of signals by formatting the signal data according to the first plurality of display parameters;
   displaying the first display data in a display device remotely located from the linear accelerator and communicatively coupled to the linear accelerator via a network;
   receiving user input responsive to the first display data in a user interface of the display device; and
   displaying diagnostic messages in a local user interface of the linear accelerator responsive to the user input,
   wherein the diagnostic messages comprise messages pre-programmed in the local user interface,
   further wherein the signal data from a diagnostic site of the plurality of diagnostic sites comprises at least one of: a frequency, an amplitude, a current, and a voltage of electric activity at the diagnostic site.

22. The method according to claim 21 further comprising executing an authorization protocol prior to performing the initializing of the scope board, wherein the method is performed only for users authorized by successfully completing the authorization protocol.

23. The method according to claim 21, wherein generating display data corresponding to selection of signals according to the first plurality of display parameters comprises:
   selecting, in the multiplexer, a plurality of signals being output from pre-defined diagnostic sites of the linear accelerator, the plurality of signals corresponding to the selection of signals;
   receiving, in the scope board, signal data corresponding to the plurality of selected signals from the multiplexer;
   converting the signal data to display data in the scope board; and
   adjusting the display data to display in a display device according to the first plurality of display parameters.

24. The method according to claim 23, wherein the signal data comprises analog data and the display data comprises digital data, further wherein converting the signal data to display data comprises converting the analog data comprising the signal data to digital data.

25. The method according to claim 21, further comprising:
   receiving, as user input, manual adjustment data corresponding to a second selection of signals and a second plurality of display parameters;
   communicating the second selection of signals to the multiplexer printed circuit board;
   communicating the plurality of display parameters and the second plurality of display parameters to the scope board; and
   displaying the second selection of signals formatted according to the second plurality of display parameters in a display device.

26. The method according to claim 21, further comprising:
   receiving, as user input, manual adjustment data corresponding to a second plurality of display parameters;
   communicating the second plurality of display parameters to the scope board; and
   displaying the selection of signals according to the second plurality of display parameters in a display device.

27. The method according to claim 21, wherein the signals of the selection of signals are comprised in a plurality of signals corresponding to measured electrical activity at a plurality of pre-defined locations in the linear accelerator.

28. The method according to claim 27, wherein generating display data corresponding to selection of signals according to the first plurality of display parameters comprises receiving measured electrical activity at the plurality of pre-defined diagnosis sites in the linear accelerator corresponding to the selection of signals over time.

29. The method according to claim 27, wherein the first plurality of display parameters comprises a region of interest of a measured electrical activity.

30. The method according to claim 29 wherein generating display data corresponding to selection of signals according to the first plurality of display parameters comprises offsetting the display data to produce a focused display of the region of interest.

31. The method according to claim 21, wherein displaying the display data in a display device remotely located from the linear accelerator comprises communicating the display data to the display device via the Internet.

32. The method according to claim 21, wherein initializing the scope board comprises setting the scope board to a default pre-set configuration.

33. The method according to claim 21, wherein initializing the multiplexer printed circuit board comprises setting the scope board to a default pre-set configuration.

34. A non-transitory computer readable medium containing program instructions embodied therein for causing a computer system to perform a facilitation of automated, electronic testing of a linear accelerator from a remote location, the program instructions comprising:
   instructions to communicatively couple, over a network, with a communications device of a remotely located linear accelerator;
   instructions to receive, as input, display data from a scope board of the remotely coupled linear accelerator through the communications device, the display data being formatted according to at least one display parameter from signal data produced at a plurality of diagnosis sites in the linear accelerator and selected as an input of a multiplexer printed circuit board coupled to the plurality of diagnosis sites;

instructions to generate a user interface, the user interface comprising:
- a plurality of buttons corresponding to the plurality of diagnosis sites, the plurality of buttons configured to receive as input a user actuation indicative of a user selection diagnosis sites from the plurality of diagnosis sites;
- a display area configured to graphically render the display data obtained from the linear accelerator according to a plurality of display parameters;
- a plurality of controls configured to receive user input responsive to the display data;

instructions to display diagnostic messages in a local user interface of the linear accelerator responsive to the user input, the diagnostic messages comprising messages pre-programmed in the local user interface, wherein signal data produced at a diagnosis site of the plurality of diagnosis sites comprises at least one of: a frequency, an amplitude, a current, and a voltage of electric activity at the diagnosis site.

35. The non-transitory computer readable medium according to claim 34, wherein the instructions to generate the user interface comprises instructions to change the display data to correspond to the user selection of diagnosis sites by selecting, in the multiplexer printed circuit board, signal data produced at signal locations of the linear accelerator corresponding to the user selection of diagnosis sites to be output from the multiplexer printed circuit board to a scope board.

36. The non-transitory computer readable medium according to claim 35, wherein the instructions to generate the user interface comprises instructions to modify the display data to comply with the user defined set of the plurality of display parameters by reformatting, in the scope board, the signal data received from the multiplexer printed circuit board to be consistent with the defined set of plurality of display parameters.

* * * * *